United States Patent
Ashihara et al.

(10) Patent No.: US 8,083,695 B2
(45) Date of Patent: Dec. 27, 2011

(54) WALK ASSISTANCE DEVICE

(75) Inventors: Jun Ashihara, Wako (JP); Yasushi Ikeuchi, Wako (JP); Hiroshi Kudoh, Wako (JP); Yutaka Hiki, Wako (JP); Tatsuya Noda, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 80 days.

(21) Appl. No.: 12/064,266

(22) PCT Filed: Mar. 30, 2007

(86) PCT No.: PCT/JP2007/057065
§ 371 (c)(1),
(2), (4) Date: Feb. 20, 2008

(87) PCT Pub. No.: WO2008/001523
PCT Pub. Date: Jan. 3, 2008

(65) Prior Publication Data
US 2009/0014042 A1    Jan. 15, 2009

(30) Foreign Application Priority Data

Jun. 29, 2006    (JP) .................................. 2006-179632

(51) Int. Cl.
*A61H 1/00* (2006.01)
*A61F 5/00* (2006.01)

(52) U.S. Cl. .................. 601/5; 601/33; 601/34; 602/16; 602/23

(58) Field of Classification Search .................... 602/16, 602/24, 26, 62; 482/66, 74; 623/33; 601/5, 601/33–35
See application file for complete search history.

(56) References Cited

U.S. PATENT DOCUMENTS

| | | | | |
|---|---|---|---|---|
| 6,024,713 A | * | 2/2000 | Barney | 602/23 |
| 6,979,304 B2 | * | 12/2005 | Nijenbanning et al. | 602/16 |
| 7,153,242 B2 | * | 12/2006 | Goffer | 482/66 |
| 7,416,537 B1 | * | 8/2008 | Stark et al. | 602/16 |
| 2006/0052732 A1 | | 3/2006 | Shimada et al. | |

(Continued)

FOREIGN PATENT DOCUMENTS

JP    07-112035    5/1995

(Continued)

*Primary Examiner* — Patricia Bianco
*Assistant Examiner* — Keri J Nelson
(74) *Attorney, Agent, or Firm* — Rankin, Hill & Clark LLP

(57) ABSTRACT

A walk assistance device capable of transmitting a force generated by a leg link to a user's trunk via a load transmit portion, wherein the leg link includes an upper first link portion connected to the load transmit portion via a first joint portion, a lower second link portion connected to a foot attachment portion via a second joint portion, a middle third joint portion connecting the first link portion to the second link portion such that a distance between the first joint portion and the second joint portion is variable, and a driving source that drives the third joint portion. The moment of inertia around the first joint portion of the leg link is reduced to decrease a load on the user's leg in walking. The driving source is disposed above the third joint portion of the first link portion so that the center-of-gravity of the entire leg link is located above the third joint portion. In the case where the driving source includes an electric motor and a reduction gear, the electric motor is disposed above the reduction gear.

7 Claims, 4 Drawing Sheets

U.S. PATENT DOCUMENTS

| | | |
|---|---|---|
| 2006/0064047 A1 | 3/2006 | Shimada et al. |
| 2008/0097269 A1* | 4/2008 | Weinberg et al. ............... 602/16 |
| 2008/0234608 A1* | 9/2008 | Sankai .............................. 601/5 |

FOREIGN PATENT DOCUMENTS

| | | | |
|---|---|---|---|
| JP | 2003-220102 | | 8/2003 |
| JP | 2004-068790 | * | 3/2004 |
| JP | 2004-236998 | | 8/2004 |
| JP | 2005-013534 | | 1/2005 |
| JP | 2005-230099 | | 9/2005 |
| JP | 2005-230207 | | 9/2005 |
| JP | 2006-043871 | | 2/2006 |
| JP | 2006-087478 | | 4/2006 |

* cited by examiner

WALK ASSISTANCE DEVICE

TECHNICAL FIELD

The present invention relates to a walk assistance device for assisting a user in walking.

BACKGROUND ART

Conventionally, a type of walk assistance device is known including a trunk attachment portion attached to a user's trunk, a thigh attachment portion attached to a thigh of a user's leg, the thigh attachment portion being connected to the trunk attachment portion via a hip joint portion corresponding to a human hip joint, a crus attachment portion attached to the crus of the user's leg, the crus attachment portion being connected to the thigh attachment portion via a knee joint portion corresponding to a human knee joint, and a foot attachment portion attached to a user's foot, the foot attachment portion being connected to the crus attachment portion via an ankle joint portion corresponding to a human ankle joint. Driving sources which drive the joint portions are provided coaxially with the joint portions, respectively (refer to Japanese Patent Laid-Open No. 2003-220102, for example). This type of walk assistance device is capable of assisting the user in walking by applying an assist moment from the driving source for the hip joint portion to the user's thigh via the thigh attachment portion, applying an assist moment from the driving source for the knee joint portion to the user's crus via the crus attachment portion, and applying an assist moment from the driving source for the ankle joint portion to the user's foot via the foot attachment portion.

Although the above conventional walk assistance device is capable of assisting all movements of the user's thigh, crus, and foot, the thigh and the crus are restrained by the thigh attachment portion and the crus attachment portion and therefore the user has an extremely constrained feeling. In addition, it is necessary to provide the driving sources for the joint portions such as the hip joint portion, the knee joint portion, and the ankle joint portion, respectively, which increases the cost disadvantageously.

In order to solve the above problem, it is conceivable to adapt the walk assistance device to include a load transmit portion, a foot attachment portion attached to the user's foot, and a leg link between the load transmit portion and the foot attachment portion, wherein a force generated by the leg link is transmitted to the user's trunk via the load transmit portion. According thereto, the walk assistance device can assist walking by reducing the load on the user's leg by means of the force from the leg link transmitted to the user's trunk via the load transmit portion. Furthermore, it is possible to reduce the constrained feeling by making the leg link free from the user's leg. In this condition, if the leg link includes an upper first link portion which is connected to the load transmit portion via a first joint portion, a lower second link portion which is connected to the foot attachment portion via a second joint portion, a middle third joint portion which connects the first link portion to the second link portion in such a way that a distance between the first joint portion and the second joint portion is variable, and a driving source which drives the third joint portion, then the load on the user's leg can be reduced by generating a force in the direction of extending the distance between the first joint portion and the second joint portion at the third joint portion by means of the driving source.

Note that the leg link is freed from the user's leg while the leg link on the side of the user's free leg (the leg whose foot is leaving the ground) swings forward with the first joint portion as a fulcrum, following the forward swing of the free leg. Therefore, in the case of increase in the moment of inertia around the first joint portion of the leg link, the user feels heavy in the leg in walking due to the moment of inertia of the leg link applied to the user's leg.

DISCLOSURE OF THE INVENTION

Problem to be Solved by the Invention

In view of the above problem, an object of the present invention is to provide a walk assistance device capable of reducing a load on the user's legs by decreasing the moment of inertia of the leg links.

Means for Solving the Problem

To achieve the above object, according to an aspect of the present invention, there is provided a walk assistance device having a load transmit portion, a foot attachment portion attached to a user's foot, and a leg link between the load transmit portion and the foot attachment portion, in which a force generated by the leg link is transmitted to a user's trunk via the load transmit portion, wherein the leg link includes an upper first link portion connected to the load transmit portion via a first joint portion, a lower second link portion connected to a foot attachment portion via a second joint portion, a middle third joint portion which connects the first link portion to the second link portion in such a way that a distance between the first joint portion and the second joint portion is variable, and a driving source which drives the third joint portion; and wherein the center-of-gravity of the entire leg link is located above the third joint portion. than the third joint portion.

According to the present invention, the center-of-gravity of the entire leg link gets closer to the first joint portion and thus the moment of inertia around the first joint portion of the leg link can be reduced. Therefore, it is possible to reduce the load on the free leg caused by the moment of inertia of the leg link when the user swings the free leg forward.

In addition, the center-of-gravity of the entire leg link located above the third joint portion means that the mass of the first link portion (the mass including the mass of accessories put on the first link portion) is greater than the mass of the second link portion (the mass including the mass of accessories put on the second link portion). Note here that the thigh of a human leg is heavier than the crus thereof. Then, the mass ratio between the first link portion and the second link portion of the leg link gets closer to the mass ratio between the thigh and the crus of the human leg by placing the center-of-gravity of the entire leg link at a position above the third joint portion. Therefore, the total natural frequency of the user's free leg and the leg link which moves following the free leg gets close to the natural frequency of the free leg alone, and accordingly the user can move the free leg without an uncomfortable feeling.

In the present invention, the driving source is preferably disposed in such a way that the center-of-gravity thereof is located above the third joint portion of the first link portion. According thereto, the center-of-gravity of the entire leg link can be located above the third joint portion by a large mass of the driving source without intentionally increasing the mass of the first link portion itself. Therefore, the moment of inertia of the leg link can be reasonably reduced without increasing the mass of the entire leg link.

Furthermore, in the case where the driving source includes an electric motor and a reduction gear, the electric motor cannot be arranged coaxially with the reduction gear due to the thickness limit of the leg link in some cases. If so, the electric motor is preferably disposed at a position above the reduction gear. More specifically, the electric motor is generally heavier than the reduction gear and therefore the moment of inertia of the leg link can be effectively reduced by placing the electric motor at a position above the reduction gear so as to bring it close to the first joint portion.

Best Mode for Carrying out the Invention

A walk assistance device according to an embodiment of the present invention will be described hereinafter. As shown in FIG. 1 and FIG. 2, the walk assistance device includes a seat member 1 as a load transmit portion which a user P sits astride, a pair of left and right foot attachment portions 2, 2 which are attached to user's left and right feet, respectively, and a pair of left and right leg links 5, 5 which are connected to the seat member 1 each via a first joint portion 3 located at the upper end and connected to the two foot attachment portions 2, 2 each via a second joint portion 4 located at the lower end.

Each leg link 5 is composed of a freely bending and stretching link which varies a distance between the first joint portion 3 and the second joint portion 4. More specifically, each leg link 5 includes an upper first link portion 6 connected to the seat member 1 via the first joint portion 3 and a lower second link portion 7 connected to each foot attachment portion 2 via a second joint portion 4, which are connected by a rotary-type third joint portion 8 in such a way that the leg link is free to bend and stretch. Each leg link 5 is equipped with a driving source 9 for the third joint 8. Then, a force in the direction of extending the distance between the first joint portion 3 and the second joint portion 4, in other words, a force in the direction of stretching each leg link 5 is applied to each leg link 5 by driving the third joint portion 8 by means of the driving source 9 to generate a supporting force which supports at least a part of the user's weight (hereinafter, referred to as a weight relief assist force). The weight relief assist force generated in each leg link 5 is transmitted to the trunk of the user P via the seat member 1 and the load on the leg of the user P is thereby reduced.

The user P can use the walk assistance device according to this embodiment only by wearing the foot attachment portions 2 on his/her feet and sitting on the seat member 1, almost having no constrained feeling. Moreover, the first joint portions 3 and the leg links 5 are located under the crotch of the user P and therefore the user P does not hit his/her hands against the first joint portions 3 or the leg links 5 when swinging his/her arms in walking, which allows free arm swing. Furthermore, the walk assistance device is compact in size and the user P can use it in a small place, by which the usability is remarkably improved in addition to the reduction in constrained feeling and the secured free arm swing.

The seat member 1 is composed of a saddle-shaped seat portion 1a which the user P sits on and a support frame 1b on the underside thereof which supports the seat portion 1a. In addition, each first joint portion 3 for each leg link 5 has an arc-shaped guide rail 31 which is longitudinal in the anteroposterior direction provided on the downside of the seat member 1. Then, each leg link 5 is movably engaged with the guide rail 31 via a plurality of rollers 62 pivotally attached to a slider 61 which is fixed to the upper end of the first link portion 6. In this way, each leg link 5 swings in the forward/backward direction around the center of curvature of the guide rail 31 and the forward/backward swing fulcrum of each leg link 5 functions as the center of curvature of the guide rail 31.

Referring to FIG. 1, the center of curvature of the guide rail 31, namely the forward/backward swing fulcrum 3a of each leg link 5 in each first joint portion 3 is located above the seat member 1. If the user P bends his/her upper body forward or the like in this condition and thereby the action point of the weight of the upper body of the user P relative to the seat member 1 is misaligned forward of the forward/backward swing fulcrum 3a of each leg link 5, the seat member 1 inclines forward and downward. If the seat member 1 continues to incline further, it is misaligned backward relative to the user P. In this embodiment, however, the action point of the weight is displaced backward under the swing fulcrum 3a along with the forward and downward inclination of the seat member 1 and thereby the anteroposterior distance between the fulcrum 3a and the action point of the weight decreases, which thereby decreases the angular moment applied to the seat member 1. Thereafter, the angular moment applied to the seat member 1 becomes zero when the action point of the weight is displaced to the position beneath the swing fulcrum 3a, which is a stable state for the seat member 1. Since the seat member 1 automatically converges on the stable state as described above, it is possible to prevent the seat member 1 from being misaligned in the forward/backward direction under the crotch of the user P.

Furthermore, the slider 61, which is located at the upper end of each leg link 5, engages with a part of the guide rail 31, which is located backward of a line between the third joint portion 8 of the leg link 5 and the forward/backward swing fulcrum 3a (the center of curvature of the guide rail 31) of the leg link 5. This secures a forward swing stroke of each leg link 5 that follows the forward swing motion of each leg of the user P without a need for increasing the length of the guide rail 31 so much.

Furthermore, the guide rails 31 for the left and right leg links 5 are pivotally supported by the support frame 1b of the seat member 1 via an anteroposterior spindle 32. Therefore, the guide rails 31 are connected to the seat member 1 so as to be free to swing in the lateral direction. The leg links 5 are therefore allowed to swing in the lateral direction, which enables the user P to abduct his/her legs.

Each foot attachment portion 2 has a shoe 21 and a joint member 22 which protrudes upward from the inside of the shoe 21. Moreover, the second link portion 7 of each leg link 5 is connected to the joint member 22 via the second joint portion 4. The second joint portion 4 is formed to a three-axis structure having a first shaft 41 extending in the lateral direction, a second shaft 42 extending in the vertical direction, and a third shaft 43 extending in the anteroposterior direction. In addition, a two-axis force sensor 44 is incorporated into the second joint portion 4. Note here that the above weight relief assist force is applied onto a line (hereinafter, referred to as reference line) L between the forward/backward swing fulcrum 3a of the leg link 5 in the first joint portion 3 and the first shaft 41 which is the forward/backward swinging fulcrum of the leg link 5 in the second joint portion 4 in profile. Then, an actual weight relief assist force applied onto the reference line L (accurately, a resultant force between the weight relief assist force and a force generated by the weights of the seat member 1 and the leg links 5) is calculated based on detected values of forces in the two-axis direction detected by the force sensors 44.

Furthermore, as shown in FIG. 1, a pair of front and back pressure sensors 24, 24, which detect loads on the metatarsophalangeal joint (MP joint) and the heel of each foot of the user P, are attached to the undersurface of an insole 23 provided in the shoe 21. In assisting walking, first, a ratio of the load applied to each foot to the total load applied to both feet of the user is calculated based on detected values of the pressure sensors 24, 24 of each foot attachment portion 2. Subsequently, a control target value of the weight relief assist force which should be generated by each leg link 5 is calculated by multiplying a preset value of the weight relief assist force by the load ratio of each foot. Then, the driving source 9 is controlled so that the actual weight relief assist force calculated based on the detected values of the above force sensor 44 reaches the control target value.

In this regard, the driving source 9 is disposed in the leg link 5, and on the other hand, the driving source 9 is a heavy load. Therefore, an increase in distance between the driving source 9 and the forward/backward swing fulcrum 3a of the leg link 5 in the first joint portion 3 also leads to an increase in distance between the center-of-gravity of the entire leg link 5 including the driving source 9 and the swing fulcrum 3a. Consequently, the moment of inertia of the leg link 5 around the swing fulcrum 3a grows, which leads to an increase in load applied to the free leg due to the moment of inertia of the leg link 5 when the user P swings the free leg (the leg off the ground) forward. Therefore, in this embodiment, the driving source 9 is disposed in such a way that the center-of-gravity is located above the third joint portion 8 of the first link portion 6 so that the center-of-gravity of the entire leg link 5 including the driving source 9 is located above the third joint portion 8. This decreases the distance between the center-of-gravity of the entire leg link 5 and the swing fulcrum 3a and reduces the moment of inertia of the leg link 5 around the swing fulcrum 3a, whereby the load on the free leg of the user P is reduced.

In addition, by having the center-of-gravity of the entire leg link 5 located above the third joint portion 8, the mass of the first link portion 6 is larger than that of the second link portion 7. Note here that the thigh of a human leg is heavier than the crus thereof. With the arrangement of the center-of-gravity of the entire leg link 5 located above the third joint portion 8, the mass ratio between the first link portion 6 and the second link portion 7 of the leg link 5 gets closer to the mass ratio between the thigh and the crus of the human leg. In addition, the length ratio between the first link portion 6 and the second link portion 7 is substantially equal to the length ratio between the thigh and the crus of the human leg. Therefore, the total natural frequency of the user's free leg and the leg link 5 which moves following the user's free leg, has a value close to the natural frequency of the free leg alone and therefore the user can move the free leg without feeling uncomfortable.

In this embodiment, the driving source 9 includes an electric motor 91 and a planetary gear type reduction gear 92. In this instance, it is conceivable that the electric motor 91 and the reduction gear 92 are disposed coaxially in the vicinity of the upper end of the first link portion 6. The lateral thickness of the leg link 5, however, is limited to prevent interference with the leg of the user P. Then, if the electric motor 91 and the reduction gear 92 are disposed coaxially with each other, the thickness of the disposed portion of the driving source 9 exceeds the thickness limit of the leg link 5 and the driving source 9 may hit the leg of the user P. Therefore, in this embodiment, the electric motor 91 and the reduction gear 92 are disposed in such a way that the electric motor 91 is located above the reduction gear 92 in the first link portion 6. Accordinqly, the electric motor 91, being heavier than the reduction gear 92, gets closer to the swing fulcrum 3a than the reduction gear 92. Therefore, the moment of inertia of the leg link 5 around the swing fulcrum 3a can be reduced effectively.

The third joint portion 8 is driven by the electric motor 91 via the reduction gear 92 and a power transmission system 10. It will be described in detail below with reference to FIG. 3. The third joint portion 8 is formed with the upper end of the second link portion 7 pivotally attached to the lower end of the first link portion 6 via a joint shaft 81 disposed laterally. Furthermore, the power transmission system 10 includes a first crank arm 101 provided on the output side of the reduction gear 92, a second crank arm 102 extending upward from the joint shaft 81 and being integrated with the second link portion 7, and a rod 103 which connects the crank arms 101 and 102 to each other. Accordingly, the rotation output of the reduction gear 92 is transmitted to the second crank arm 102 via the first crank arm 101 and the rod 103, the second link portion 7 swings around the joint shaft 81 with respect to the first link portion 6, and the leg link 5 is bent as shown in FIG. 4 from the extended condition shown in FIG. 1.

However, if the leg link 5 is bent while the leg of the user P is extending straight, the third joint portion 8 protrudes forward of the knee joint of the user P and imparts an uncomfortable feeling to the user P. Therefore, when the leg of the user P extends straight, it is desirable that the joint shaft 81 of the third joint portion 8 is located on the reference line L so that the flexion angle θ of the third joint portion 8 is zero degrees. In other words, the leg link 5 is extended as shown in FIG. 1.

In this regard, if the leg link 5 is a simple bending and stretching link, the extension speed of the leg link 5, which is obtained by differentiating the length of a line segment between the swing fulcrum 3a of the leg link 5 in the first joint portion 3 and the first shaft 41 of the second joint portion 4 with respect to the flexion angle θ of the third joint portion 8, becomes zero when the flexion angle θ becomes zero degrees. Therefore, if the flexion angle θ becomes zero degrees, the walk assistance device loses the ability to control in the direction of extending the leg link 5. In other words, in the direction of pushing up the seat member 1. Accordingly, even if there is an increase in the weight relief assist force, which should be generated in the leg link 5 on a standing leg side due to a shift from a state where the user P stands upright on two legs to another state where the user P stands on one leg, it is impossible to appropriately control the weight relief assist force if the standing leg extends straight and the third joint portion 8 of the leg link 5 on the standing leg side has a zero degree of the flexion angle θ.

Therefore, in this embodiment, the second link portion 7 of the leg link 5 is telescopically formed by a cylindrical upper half portion 71 connected to the third joint portion 8 and a lower half portion 72 slidably inserted into the upper half portion 71 and supported thereby, and it is further provided with an interlock system 11 which extends and retracts the second link portion 7 in conjunction with the operation of increasing and decreasing the flexion angle θ of the third joint portion 8. Then, the interlock system 11 is adapted so that the extension speed of the second link portion 7 does not become zero even if the flexion angle θ is brought to zero degree where the extension speed is obtained by differentiating the length of the second link portion 7 with respect to the flexion angle θ of the third joint portion 8.

Accordingly, the extension speed of the leg link 5 does not become zero when the flexion angle θ is zero degrees. Therefore, even if the flexion angle θ becomes zero degrees, the ability to control in the direction of pushing up the seat member 1 is maintained and the weight relief assist force can be appropriately controlled in response to a change in load. Consequently, it becomes possible to cause the flexion angle of the third joint portion 8 to be zero degrees with the leg of the user P extending straight. In other words, to cause the leg link 5 to be extended, and therefore allow the user P to use the walk assistance device without feeling uncomfortable. The lower half portion 72 is adjustable to an arbitrary length by using a lock nut 73. Therefore, the leg link length can be adjusted in response to the length of the leg of the user P.

In this regard, it is also possible to provide a driving source for extension and retraction of the second link portion 7 which moves the lower half portion 72 of the second link portion 7 up and down with respect to the upper half portion 71 and a sensor for detecting the flexion angle θ of the third joint portion 8 in order to form an interlock system so that the lower half portion 72 of the second link portion 7 is moved up and down by actuating the driving source for extension and retraction according to a signal from the sensor. This, however, increases the cost and the total weight of the leg link due to the effect of the driving source for extension and retraction. Therefore, in this embodiment, the interlock system 11 is formed by a mechanical system which converts the rotary motion around the third joint portion 8 of the upper half portion 71 of the second link portion 7 with respect to the first link portion 6 to a linear motion of the lower half portion 72 of the second link portion 7 so as to reduce the cost and to hold down the increase in the total weight of the leg link 5.

The interlock system 11 more specifically includes a first interlocking link 112 with one end pivotally mounted on the upper half portion 71 of the second link portion 7 by a shaft 111, a second interlocking link 115 with one end pivotally mounted on the lower half portion 72 of the second link portion 7 by a shaft 113 and the other end pivotally mounted on the other end of the first interlocking link 112 by a shaft 114, and a third interlocking link 118 with one end pivotally mounted on the first link portion 6 by a shaft 116 and the other end pivotally mounted on the middle portion of the first interlocking link 112 by a shaft 117. According thereto, a quadrilateral shape, which is formed by the joint shaft 81 of the third joint portion 8, the shaft 111, the shaft 117, and the shaft 116, deforms by a displacement of the shaft 111 caused by the rotary motion around the third joint portion 8 of the upper half portion 71 of the second link portion 7 with respect to the first link portion 6 and this deformation causes a change in an angle between a line segment connecting the shaft 114 to the shaft 111 and a line segment connecting the shaft 114 to the shaft 113. This change in the angle causes a change in distance between the shaft 111 and the shaft 113 and thereby the lower half portion 72 of the second link portion 7 linearly moves in a longitudinal direction (vertical direction) of the upper half portion 71 with respect thereto. If the flexion angle θ of the third joint portion 8 decreases, the lower half portion 72 moves downward as shown in FIG. 1 and thereby the length of the second link portion 7 increases. If the flexion angle θ increases, the lower half portion 72 moves upward as shown in FIG. 4 and thereby the length of the second link portion 7 decreases. Note that the interlock system 11 is not limited to the link mechanism of this embodiment, but it can be formed by a cam mechanism or a rack and pinion mechanism.

Where the first joint portion 3 is formed into one having an arc-shaped guide rail 31 as described above, a space is generated between the guide rail 31 and the seat member 1 on the underside thereof. Therefore, in order to use the space effectively, a battery 12 for the driving source 9, a controller 13, and a motor driver 14 are disposed in the support frame 1b of the seat member 1 in such a way as to fit into the space between the seat member 1 and the guide rail 31.

In this regard, it is desired that the driving source 9, which is a heavy load, is disposed in a position higher than the third joint portion 8 in order to reduce the moment of inertia around the swing fulcrum 3a in the first joint portion 3 of the leg link 5. Therefore, in this embodiment the driving source 9 is disposed in a position above the third joint portion 8 of the first link portion 6 as described above. Furthermore, the battery 12, which is a heavy load, is also disposed in the seat member 1 above the third joint portion 8. If the driving source 9 and the battery 12 are located in higher positions in this manner, the weight of the driving source 9 and that of the battery 12 easily generate a forward/backward tilting moment around the first shaft 41 of the second joint portion 4 in the leg link 5 in the state where the user P stands upright, and the tilting moment causes a forward/backward pushing force to be applied to the seat member 1.

Therefore, in this embodiment, the walk assistance device is adapted to prevent the tilting moment from being generated. In this connection, the condition of the leg link 5 in which the user P stands upright is defined as a normal condition (the condition shown in FIG. 1) in the following description. In the normal condition of the leg link 5, the driving source 9 and the battery 12 which are heavy loads are disposed in such a way that a plane, which is vertical and parallel to the lateral direction and passes through the first shaft 41 of the second joint portion 4, in other words, a frontal plane (in this embodiment, the frontal plane substantially matches the above reference line L) passes through the anteroposterior width of the driving source 9 and the anteroposterior width of the battery 12. This reduces an anteroposterior offset distance of the center-of-gravity of the driving source 9 and that of the center-of-gravity of the battery 12 with respect to the above frontal plane. Therefore, in the normal condition of the leg link 5, the arrangement reduces the anteroposterior tilting moment around the first shaft 41 of the second joint portion 4 generated in the leg link 5 by the weight of the driving source 9 and that of the battery 12. Consequently, the anteroposterior pushing force applied to the seat member 1 due to the tilting moment is also reduced in the state where the user P stands upright, thereby improving the stability.

It is also possible to dispose the battery 12 in the first link portion 6 of the leg link 5. If, however, the battery 12 is disposed in the seat member 1 as described in this embodiment, the mass of the battery 12 is not added to the leg link 5 and therefore the moment of inertia of the leg link 5 can be reduced as much as possible advantageously.

Although the embodiment of the present invention has been described hereinabove with reference to the drawings, the present invention is not limited thereto. For example, while both of the electric motor 91 and the reduction gear 92 which form the driving source 9 are disposed above the third joint portion 8 of the first link portion 6 in the above embodiment, it is also possible to dispose the reduction gear 92 coaxially with the third joint portion 8 and the electric motor 91 in a position above the third joint portion 8 of the first link portion 6. Also in this case, the total center-of-gravity of the electric motor 91 and the reduction gear 92, namely the center-of-gravity of the driving source 9 is located above the third joint portion 8 of the first link portion 6.

In addition, although each leg link 5 is formed by an extendable and retractable link having a rotary-type third joint portion 8 in the middle of the leg link 5 in the above embodiment, alternatively the leg link can be formed by an extendable and retractable link having a direct-acting type third joint portion. Moreover, although the first joint portion 3 has the arc-shaped guide rail 31 and the forward/backward swing fulcrum 3a of each leg link 5 in the first joint portion 3 is located above the seat member 1 in the above embodiment, the first joint portion 3 can be formed by a simple-structured joint portion having a lateral shaft pivotally supporting the upper end portion of each leg link 5 so as to be free to swing in the anteroposterior direction. Furthermore, the load transmit portion can be formed by a harness to be attached around the user's waist. Moreover, to assist a user who is handicapped in one leg due to a fracture or the like of the leg in walking, it is possible to leave only the leg link on the side of the user's handicapped leg of the left and right leg links 5, 5 in the above embodiment while removing the other leg link.

DESCRIPTION OF REFERENCE NUMBERS

Figure 1:
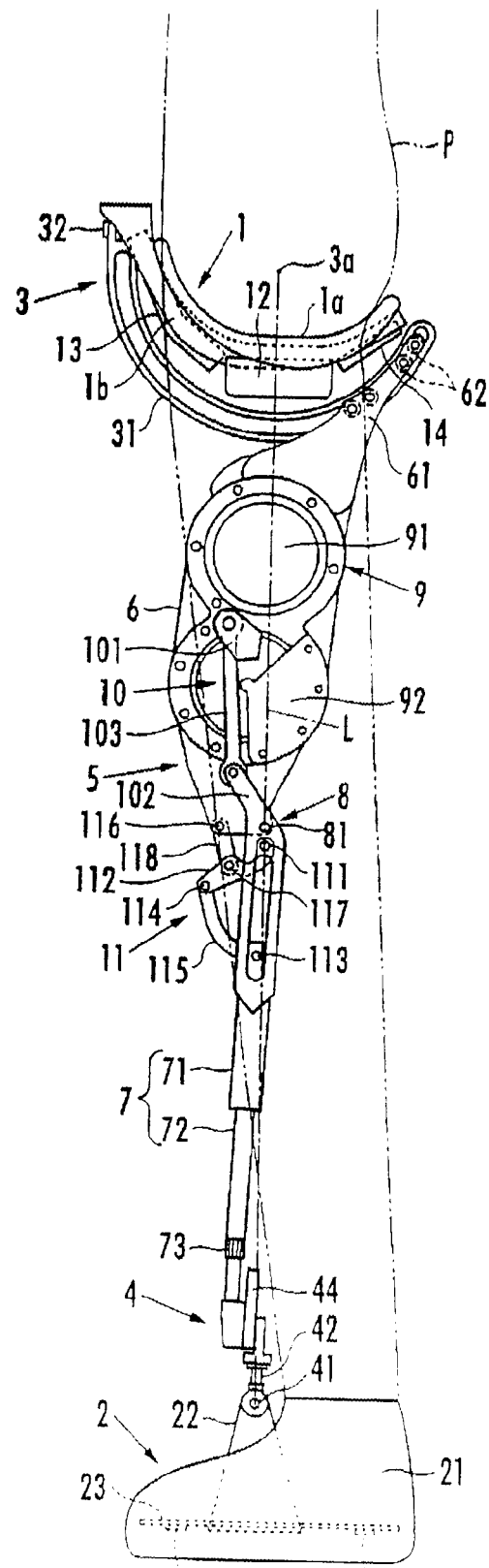
FIG. 1 is a side view of a walk assistance device according to an embodiment of the present invention.
Figure 2:
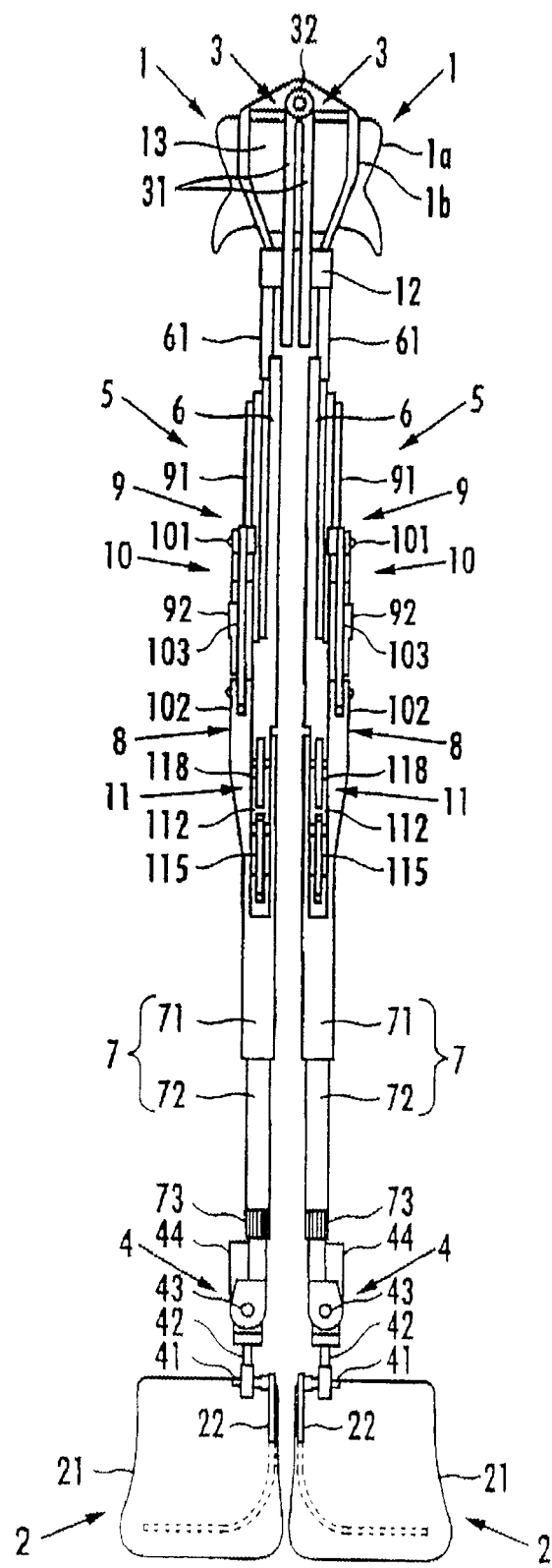
FIG. 2 is a front view of the walk assistance device according to the embodiment.
Figure 3:
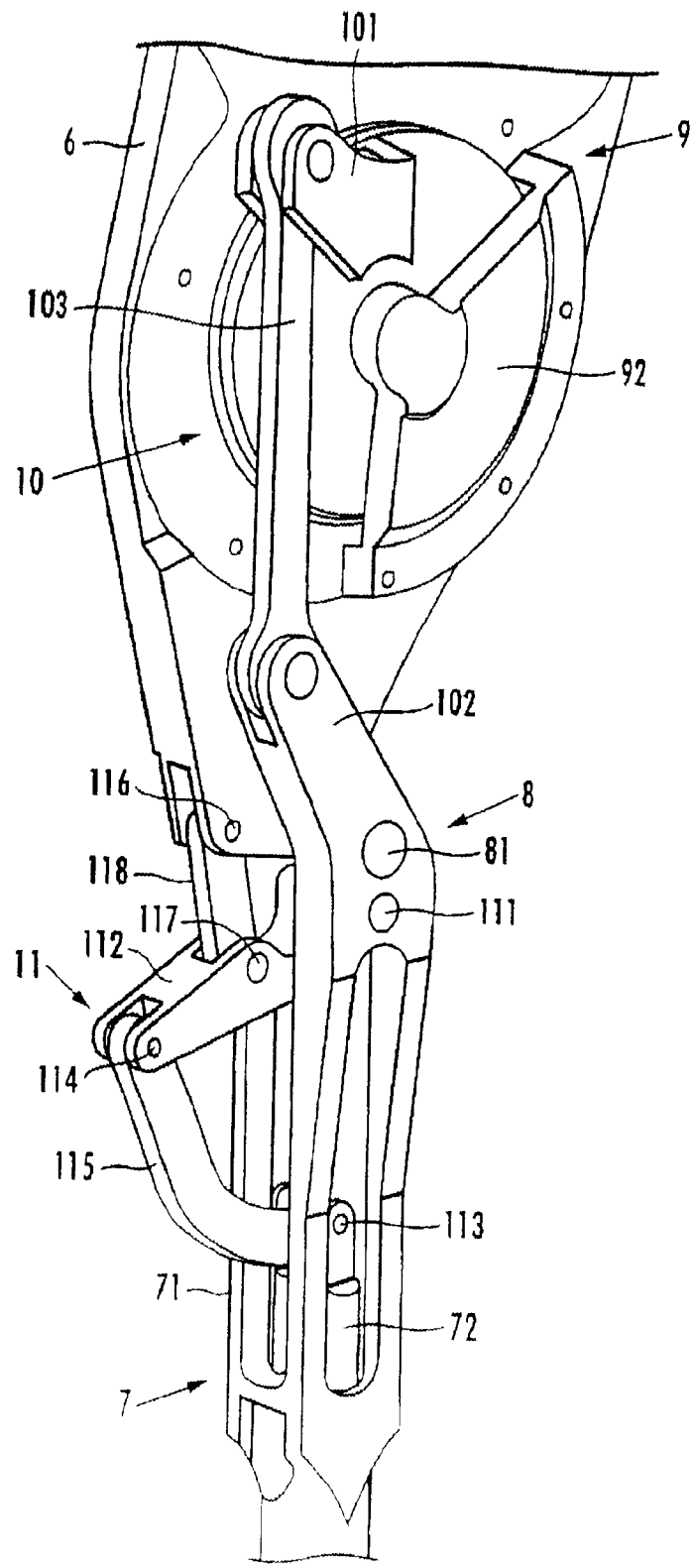
FIG. 3 is a perspective diagram of components in the vicinity of a third joint portion of a leg link of the walk assistance device according to the embodiment.
Figure 4:
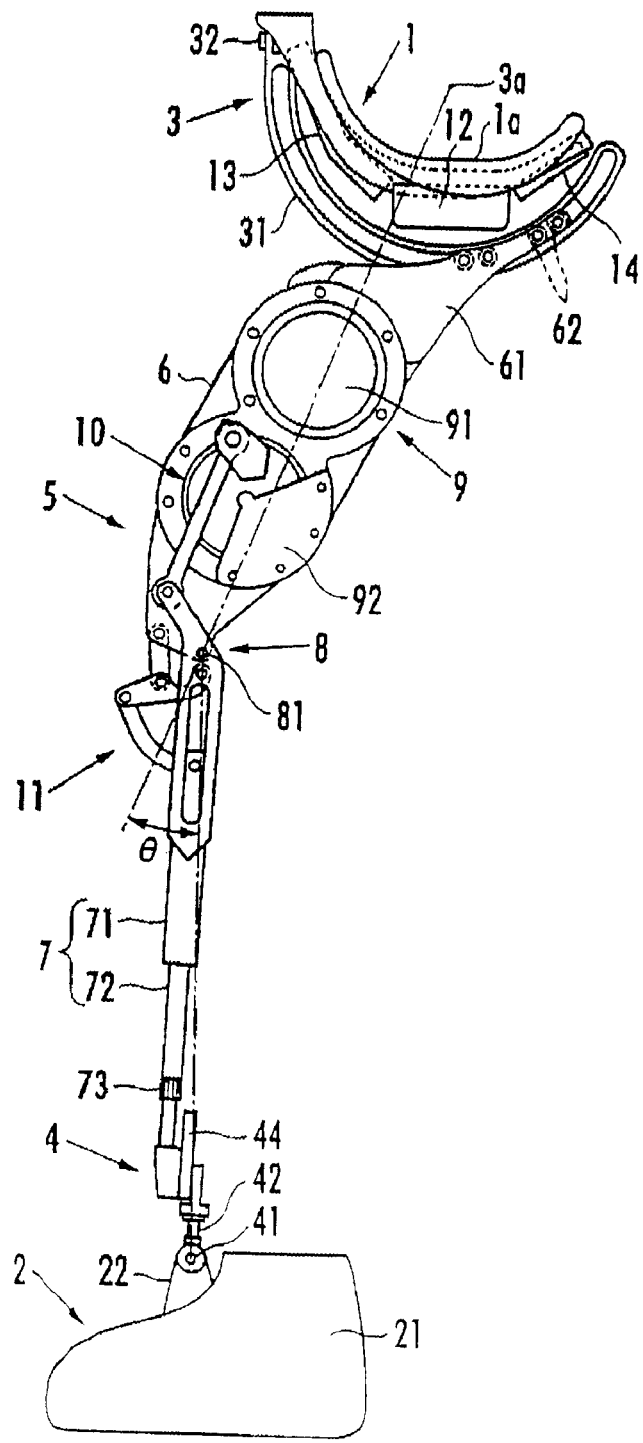
FIG. 4 is a side view of the leg link of the walk assistance device in a state where it is bent according to the embodiment.

1 Seat member (Load transmit portion)
2 Foot attachment portion
3 First joint portion
4 Second joint portion
5 Leg link
6 First link portion
7 Second link portion
8 Third joint portion
9 Driving source
91 Electric motor
92 Reduction gear
91 Electric motor
92 Reduction gear

The invention claimed is:

1. A walk assistance device having a load transmit portion, a foot attachment portion attachable to a user's foot, and a leg link between the load transmit portion and the foot attachment portion, in which a force generated by the leg link is transmitted to a user's trunk via the load transmit portion,
wherein the leg link includes an upper first link portion connected to the load transmit portion via a first joint portion, a lower second link portion connected to the foot attachment portion via a second joint portion, a middle third joint portion connecting the first link portion to the second link portion such that a distance between the first joint portion and the second joint portion is variable;
wherein a driving source is directly attached to the first link portion and mechanically connected to the third joint portion so as to drive the third joint portion;
wherein the center-of-gravity of the entire leg link is above the third joint portion;
wherein the driving source includes an electric motor and a reduction gear, and wherein the reduction gear and the electric motor are disposed on the first link portion and the reduction gear is located between the electric motor and the third joint portion such that the reduction gear is closer to the third joint portion than the electric motor, and the electric motor is spaced from the third joint portion along the first link portion.

2. The walk assistance device according to claim 1, wherein the driving source is disposed such that the center-of-gravity thereof is higher than the third joint portion of the first link portion.

3. The walk assistance device according to claim 1, wherein the driving source further comprises a power transmission system operably connecting the reduction gear to the third joint portion, the power transmission system comprising:
a first crank arm projecting from the reduction gear;
a second crank arm projecting from the leg link adjacent to the third joint portion; and
a rod connecting the first crank arm to the second crank arm.

4. The walk assistance device according to claim 3, wherein the second crank arm is integrally formed with the second link portion and projects from an upper portion adjacent to the third joint portion of the second link portion.

5. The walk assistance device according to claim 1, wherein the load transmit portion is a saddle-type seat adapted for a user to sit astride.

6. The walk assistance device according to claim 1, wherein a mass of the first link portion is greater than a mass of the second link portion.

7. The walk assistance device according to claim 1, wherein the second link portion has a variable length that changes upon a rotation about the joint portions such that the distance between the first joint portion and the second joint portion changes during operation of the walk assistance device.

* * * * *